United States Patent [19]

Malmquist

[11] Patent Number: 5,273,907
[45] Date of Patent: Dec. 28, 1993

[54] METHOD AND MEANS FOR PERFORM BIOCHEMICAL REACTIONS

[76] Inventor: Mats Malmquist, Hurtigs gata 63, S-754 39 Uppsala, Sweden

[21] Appl. No.: 932,122

[22] Filed: Aug. 19, 1992

Related U.S. Application Data

[63] Continuation-in-part of Ser. No. 700,826, May 16, 1991, abandoned.

[30] Foreign Application Priority Data

May 16, 1990 [SE] Sweden .................. 9001772

[51] Int. Cl.$^5$ .................. G01N 9/30; G01N 21/03; C12M 1/24; C12M 1/18
[52] U.S. Cl. .................. 436/165; 436/180; 435/287; 435/296; 435/299; 435/300; 220/507; 422/60; 422/72; 422/100
[58] Field of Search .................. 422/59, 60, 72, 99, 422/100; 435/91, 287, 296, 299, 300; 436/165, 177, 180; 210/360.1, 512.1, 789; 494/16, 20; 73/864.02, 863.21; 206/443; 220/507; 405/259.6

[56] References Cited

U.S. PATENT DOCUMENTS

| | | | |
|---|---|---|---|
| 4,028,930 | 6/1977 | Moreno | 206/443 |
| 4,092,113 | 5/1978 | Hardy | 422/72 |
| 4,104,025 | 8/1978 | Retzer | 422/72 |
| 4,123,224 | 10/1978 | Givnei et al. | 422/59 |
| 4,690,670 | 9/1987 | Nielsen | 494/16 |
| 4,954,264 | 9/1990 | Smith | 210/782 |
| 4,956,298 | 9/1990 | Diekmann | 430/311 |
| 5,069,336 | 12/1991 | Mauthe | 220/507 |

FOREIGN PATENT DOCUMENTS

225788 8/1985 German Democratic Rep. .

*Primary Examiner*—Robert J. Warden
*Assistant Examiner*—T. A. Trembley
*Attorney, Agent, or Firm*—Browdy and Neimark

[57] ABSTRACT

The present invention relates to a method for performing biochemical reactions and a combination of a capillary (3) and a reaction vessel (1) for use in said method. The reagent capillaries (3) contain frozen reagents (6-13) separated from each other by air or an inert fluid. At use, the reagent capillaries (3) are placed in a reaction vessel (1) to be thawed and then the contents are centrifugated to the bottom of the reaction vessel (1). The invention is intended for use in all types of biochemical standard reactions and diagnostic tests in which the reagents cannot be mixed in advance. It is particularly suitable for PCR diagnostics but is also especially beneficial when handling radioactive reagents, e.g. labeled nucleotides, for sequencing reactions, etc.

16 Claims, 5 Drawing Sheets

METHOD AND MEANS FOR PERFORM BIOCHEMICAL REACTIONS

The present application is a continuation-in-part of application Ser. No. 07/700,826, filed May 16, 1991 now abandoned, which is hereby incorporated by reference in the entirety.

FIELD OF THE INVENTION

The present invention relates to a method for performing biochemical reactions and a combination of a capillary and a reaction vessel for use in said method.

The invention is applicable for all small volume biochemical reactions in which the reagents cannot be mixed beforehand. Particularly, the invention is intended for the PCR (Polymerase Chain Reaction)-technique.

BACKGROUND OF THE INVENTION

The recently developed PCR-technique has led to great advances in a number of important diagnostic sectors, e.g. the diagnosis of many different diseases, determinations of paternity, forensic medicine, etc. When it is desired to detect RNA, a necessary preliminary stage is the conversion of the RNA into DNA by means of the enzyme reverse transcriptase. The diagnosis of AIDS is routinely made by the detection of antibodies to the HIV-virus in the blood by means of an ELISA (Enzyme Linked ImmunoSorbent)-test. A person may, however, be HIV-positive without antibodies being present if he/she, for instance, is in the early stages of the disease. In this case the ELISA test gives a negative result and the person concerned then risks unwittingly transmitting the infection to others. Therefore the need for a better, i.e. more sensitive, HIV test is very great. The diagnosis of other viruses, also, the culture of which previously took a long time, has been improved with the PCR technique.

As regards the practical procedure, PCR diagnosis comprises three stages:

1) preparation of the reaction mixtures, i.e. preparation of the samples to be tested;

2) the actual amplification, i.e. the chain reaction in which the DNA molecules are replicated exponentially; and 3) the detection of positive samples by means of electrophoresis or hybridisation.

A disadvantage of the PCR method which the present inventor aims to eliminate is that stage 1) is time-consuming and demanding work, primarily because the reagents cannot be mixed in advance, and thus gives rise to many sources of error. It is very important that stage 1) should be carried out with great care and precision because the amplification in stage 2) and the detection result in stage 3) depend absolutely on the reliability of stage 1).

During the various stages of preparing the reagents for a biochemical reaction, such as PCR mentioned above, there is a risk of cross-contamination between the different reaction vessels or test tubes.

While preparing for a PCR reaction there is also a risk of so-called "carry-over contamination" from the person who handles the sample. This applies especially to routine analysis to detect a specific DNA if the same person carries out all the stages before PCR reaction and also handles the PCR product. On skin, hair and laboratory clothing there may be remnants of PCR products from amplifications carried out previously which engender "false" positive results. The risk of false positive results increases the more sensitive the test. The test for HIV is very sensitive and it need scarcely be said that a false positive result causes needless distress to the individual notified of it.

SUMMARY OF THE INVENTION

The object of the invention was to diminish the contamination risk as well as the time required to prepare small reagent volumes for a specific biochemical reaction in which the reagents cannot be mixed in advance and the preparation is time-consuming.

This object is achieved by a method using a combination of a reagent capillary and a reaction vessel, the reagent capillary being filled with reagents which are maintained separate from each other, and said reaction vessel having a bore therein into which one capillary can be inserted.

When the reagent capillary is inserted into a first bore in a lid of the reaction vessel, the reaction vessel with capillary inserted therein is centrifugated to bring the contents of the reagent capillary to the bottom of the reaction vessel. Sample is then added to the reaction vessel. The sample may be added by inserting a capillary containing a sample to be tested into a second bore in the lid of the reaction vessel, and centrifuging the reaction vessel.

In one embodiment of the invention, the reagents are provided in frozen form and are thawed prior to being inserted into the first bore.

In another embodiment, the reagent capillary is provided with a protective cover on the upper end thereof, and a locking groove on the lower end thereof. The reagent capillary is then inserted into the bore of the reaction vessel until the locking groove of the lower end of the lower end engages with the ends of the bore of the reaction vessel.

In yet another embodiment of the present invention, the bore is covered by a permeable membrane, and the reagent capillary is inserted through the permeable membrane into the bore.

In DD-A1-225 788 a capillary is described, which contains several reagents separated by intermediate hydrophobic liquid, e.g. paraffines, oils, alkanes. In this capillary, reagent storage as well as sample reaction takes place. The sample is added to the capillary and then the capillary is melted at one end. The mixing of the sample with the reagents is effected by placing a steel pin into the capillary and moving a magnet in an upward and downward direction along the outside of the capillary. After a suitable incubation period the capillary is centrifugated to obtain the reaction solution and the hydrophobic liquid in two separate phases. To be able to analyze the reaction solution the capillary has to be cut at the sealed end and also at the boundary between hydrophobic liquid-reaction solution and thereafter the reaction solution is transferred to a cuvette or the like, for measurement of, for example, UV absorbance.

This known capillary solves the problem of preparing reagents which cannot be prepared in advance. However, because of the above mentioned handling stages, there is no time saving nor reduction of contamination compared to conventional pipetting techniques.

BRIEF DESCRIPTION OF THE DRAWINGS

The invention will now be described in greater detail below with reference to the accompanying drawings in which.

DETAILED DESCRIPTION OF THE INVENTION

Figure 1:
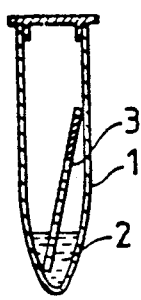
FIG. 1 is a diagrammatic view of a reaction vessel including a reagent capillary containing reagent.

FIG. 1 shows a ready-prepared reaction vessel 1 according to the present invention. Inside the reaction vessel 1, for instance an Eppendorf tube, is placed a reagent capillary 3. The reagent capillary 3 is provided with different reagents, which can be of any suitable type for a desired reaction. In the bottom of the reaction vessel 1 there may be water or buffer 2 for subsequent dilution of the reagents.

Figure 2:
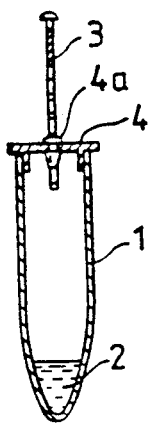
FIG. 2 is a diagrammatic view of an alternative embodiment of a reaction vessel including an alternative embodiment of a reagent capillary.
Figure 3:
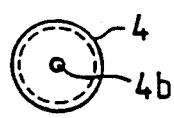
FIG. 3 is a plan view of the embodiment shown in FIG. 2.

FIG. 2 shows an alternative and preferred embodiment of a reaction vessel 1 and a reagent capillary 3. The reaction vessel 1 is provided with a lid 4 having a bore 4a. The bore 4a is covered by a permeable membrane 4b. The bore 4a fitted with a membrane is located centrally in the lid 4 in the shown embodiment but this is not a critical feature. In fact it is possible to provide the lid with several bores to be able to put in more than one reagent capillary as desired. The bore 4a forms a stop collar for the reagent capillary 3 in accordance with FIG. 5, which is described in greater detail below.

Figure 4:
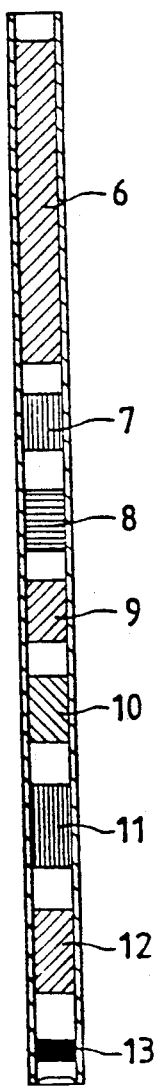
FIG. 4 shows the reagent capillary depicted in FIG. 1 on a larger scale.

The reagent capillary 3 depicted in FIG. 4 is designed to be inserted into the reagent vessel 1 shown in FIG. 1. The reagent capillary 3 is provided with different reagents 6-13 for a specific biochemical reaction. The amount of each reagent is calculated and intended only for this specific reaction. If a PCR reaction is to be performed the reagent solutions 6-13 comprise PCR buffer, dCTP, dGTP, dATP, dTTP, two or more oligonucleotides, all of the reagents being calculated for a specific PCR reaction, and thermostable DNA polymerase. Between the reagents there is air or an inert fluid. Naturally, the mutual order is optional.

Figure 5:
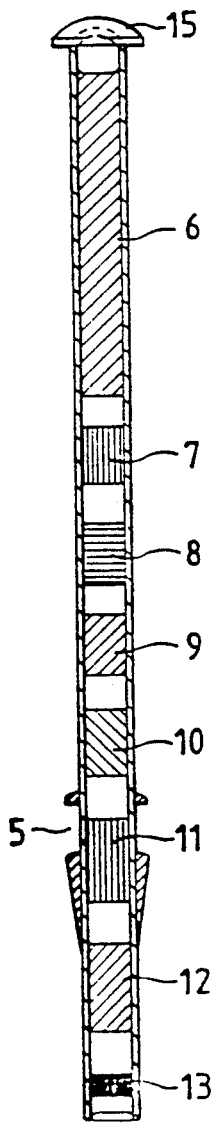
FIG. 5 shows the reagent capillary depicted in FIG. 2 on a larger scale.

A modified reagent capillary is depicted in FIG. 5. This reagent capillary is designed to be inserted into a reaction vessel according to FIG. 2. The reagent capillary differs from the reagent capillary shown in FIG. 4 in that there is an annular locking groove 5 on the lower part of the capillary intended to be snapped into the bore 4a. Moreover, a protective cover 15 is fitted over the upper end of the capillary. The reaction vessel according to FIG. 2 and the reagent capillary according to FIG. 5 are stored separately until use. Upon use, the lower end of the capillary 3 is pushed through the permeable membrane 4b in the lid 4 of the reaction vessel 1, whereupon the locking groove 5 engages with the stop collar formed by the bore 4a. The protective cover 15 protects the contents of the reagent capillary 3 from contamination during the process of insertion and pushing into the reaction vessel 1. When the reagent solutions in the reagent capillary 3 have thawed, they are then centrifuged down and mixed with one another and, where applicable, with the diluent 2 at the bottom of the vessel 1. After centrifuging, the lid 4 may be opened without having to remove the capillary 3 from the lid. The advantage of this is that material can readily be added to or extracted from the reaction vessel if desired.

After producing the reagent capillaries, i.e. by aspirating the different reagents with air or inert fluid in between, either manually or automatically, they may be packed separately or placed in a reaction vessel in kits for performing a specific biochemical reaction. Of course, this packaging takes place under sterile conditions.

An alternative method of producing the capillaries is to aspirate the reagents into capillaries with air or inert fluid between the reagents, freeze the capillaries, cut the capillaries in the air sections, and to place the desired capillary pieces in one common outer capillary having an inner diameter corresponding to the outer diameter of the capillary pieces. This would allow combining of the reagents in any desired way.

Figure 6:
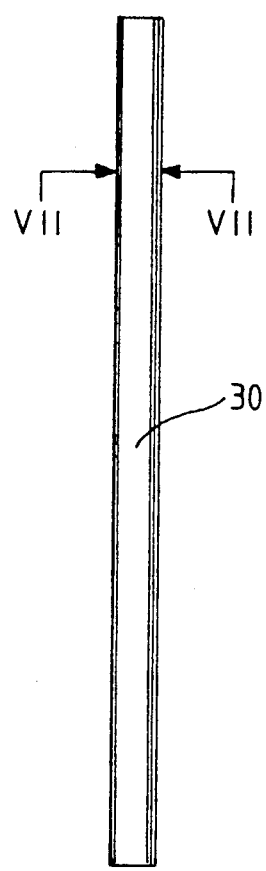
FIG. 6 shows an alternative embodiment of the reagent capillary.
Figure 7:
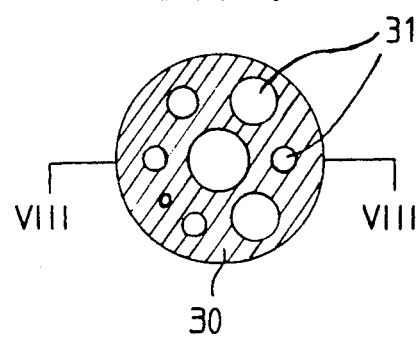
FIG. 7 is a cross section along line VII—VII in FIG. 6.
Figure 8:
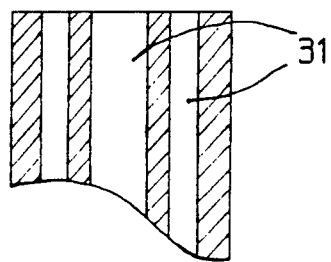
FIG. 8 is a cross section along line VIII—VIII in FIG. 7.

In FIG. 6 there is shown a reagent capillary 30 comprising several longitudinal capillaries 31 each having a smaller diameter than the reagent capillary 3 above. In this case, the thin capillaries 31 each comprise a single reagent. Thus, the reagents are not arranged vertically, like in the previous Figures, but horizontally and are not separated from each other by air or an inert fluid but by the material of the thin capillary walls, e.g. plastic. The thin capillaries can be provided in a multi lumen tube, which is best shown in the cross section of FIG. 7. Alternatively the capillaries can be provided as separate capillaries bonded to a bundle. The bonding can be achieved by, for example, heating or adhesive. As shown in FIGS. 7-8, the diameters of capillaries 31 are varied in relation to each other to contain different volumes. Another parameter influencing the volume is the length of capillary 30. If the capillary volumes are inadequate for specific reagent volumes then, in addition to varying the diameter and length of the capillaries, it is also possible to vary the concentration of the reagents.

The embodiments according to FIGS. 6-8 simplifies production and reduces production costs. Capillaries 30 of preferred material, such as glass or plastic, are produced with as many lumens as the number of reagents to be included in the thin capillaries. The lumens are separated from each other by the material, and each lumen should contain one reagent. The inner diameter of each lumen is chosen to correspond to the volume of the reagent it is to contain. In the manufacturing procedure of reagent capillaries, the multi lumen tube is cut into segments of specific lengths. The relative amounts of reagents are thus determined by the inner diameter of lumens, and the absolute amounts of reagents are determined by the segment lengths. One individual segment may then be used as a reagent capillary according to the invention, or may be arranged within an external sheath with optimal performance with respect to fitting into the lids of reaction vessels, with respect to stable behavior in the microcentrifuge etc. In the latter case, the sheath with included segments is used as a reagent capillary according to the invention.

Figure 9:
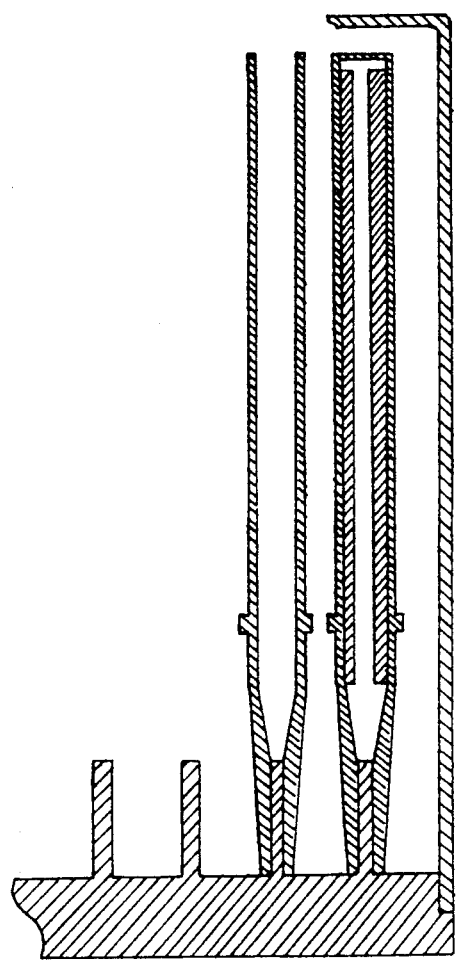
FIG. 9 is a cross sectional view of a kit for storing reagent capillaries.

Finally, FIG. 9 shows a kit or holder 32 for reagent capillaries 33. The kit comprises a bottom portion 34 of suitable shape provided with pegs 35 extending upwards from the bottom. Furthermore, the kit is provided with an upper lid or cover 36, the side walls of which engage with the bottom 34 in an outer peripheral portion thereof. The reagent capillaries 33 have a lower, tapered tip 37 inserted over the pegs so that the pegs now are inside the tips. The reagent capillaries can be directly provided with reagents or with an inner capillary 38 filled with reagents. After providing the reagents, the capillaries are optionally sealed in the upper end.

The reagent capillaries with or without the reaction vessels are stored in the frozen state until use. For use the reagent capillary is thawed and the contents thereof are centrifuged down in the reaction vessel, being mixed with each other and with diluent if any. If a PCR reaction is to be performed, all the reagents, including heat stable DNA polymerase, are now in the reaction vessel and the only further addition needed before the amplification is of the sample, e.g. blood.

Preferably the sample is added by using a dosing system described in applicant's pending Swedish patent application SE 91 0726-0. Briefly, the sample is drawn up into a capillary, of the same type as reaction capillary 3, by capillary effects. Thereafter the sample capillary is inserted in an unoccupied bore 4a in the lid 4 of the reaction vessel 1 which thereafter is once again centrifugated.

For fast detection of the results of the amplification reaction, the present inventor suggests using material for the reaction vessels that does not, or only slightly, absorb UV light. If ethidium bromide is added after the reaction it would then be possible to detect whether or not DNA has been amplified by viewing the vessels under UV light with the naked eye. Preferably the ethidium bromide addition is made in the same manner as the above described sample addition.

It should be appreciated the the shown reagent capillaries 3 have been prepared for a specific sample volume and a specific biochemical reaction. Other reactions require different volumes and number of reagents.

According to the present invention numerous factors are obviated, e.g. pipetting, changing pipette-tips, changing gloves, repeated opening and closing of the reaction vessel, whereby the number of sources of error is substantially reduced and the tests are more reliable, quicker and cheaper. The problem of false positive results with PCR is thus appreciably reduced.

Thus the invention offers the biotechnical industry the chance to supply a new type of "kits", i.e. complete sets containing reagents for a specific reaction. Large numbers of such kits are on the market today; they usually consist of Eppendorf tubes containing different reagents suitable for about 100 standard reactions. For each reaction a certain volume is mixed from each tube. With the aid of reagent capillaries one kit can contain, e.g. 500 capillaries, each ready to use for the reaction it is designed for. The advantage of kits based on the reagent capillaries described in the present application is that the user does not have to pipette the reagent and is able, instead, to select the appropriate reagent capillary for the relevant reaction with fingers or tweezers. The simplification of the work is obvious, above all in regard to the handling of radioactive reagents, as there is no risk of contaminating pipettes, less risk of radioactive waste and shorter periods of exposure for the staff. In addition to the economic and operational advantages of reaction capillaries in PCR technology, there is the saving in time and the benefits of worker protection in many biotechnological sectors.

I claim:

1. A method for performing biochemical reactions in which the reagents cannot be mixed in advance, comprising:
   providing a reagent capillary which is filled with reagents separated from each other;
   inserting said reagent capillary into a first bore in a lid of a reaction vessel having at least one bore therein;
   centrifugating said reaction vessel with capillary inserted therein to bring the contents of said reagent capillary to the bottom of said reaction vessel; and
   adding sample to be reacted to said reaction vessel.

2. The method according to claim 1, further comprising inserting a capillary containing a sample to be tested into a second bore in said lid of said reaction vessel, and centrifuging said reaction vessel.

3. The method according to claim 1, wherein said reagents are provided in frozen form and are thawed prior to being inserted into said first bore.

4. The method according to claim 1, wherein said reagent capillary is provided with a protective cover on the upper end thereof and a locking groove on the lower end thereof, and said reagent capillary is inserted into said first bore until said locking groove engages with the edges of said first bore.

5. The method according to claim 4, wherein said first bore is covered by a permeable membrane and said reagent capillary is inserted through said permeable membrane into said first bore.

6. A combination of a reagent capillary and a reaction vessel comprising a reagent capillary having an upper and lower end and containing different reagent solutions in predetermined volumes separated from each other; and
   a reaction vessel comprising a lid provided with at least one bore;
   whereby said different reagent capillary is of such diameter that it can be inserted into said at least one bore.

7. The combination according to claim 6 wherein said reagent solutions are in frozen form.

8. The combination according to claim 6, wherein said reagent capillary is provided with a locking groove at the lower end thereof and a protective cover at the upper end thereof.

9. The combination according to claim 6, wherein said at least one bore is covered by a permeable membrane.

10. The combination according to claim 6, wherein said different reagent solution comprise at least one nucleic acid and/or at least one enzyme for a specific reaction.

11. The combination according to claim 10, wherein said different reagent solution comprise PCR buffer, dCTP, dGTP, dATP, dTTP, two or more oligonucleotides specific for a specific PCR reaction, and thermostable DNA polymerase.

12. The combination according to claim 6, wherein said reaction vessel is made of a material that substantially does not adsorb ultraviolet light.

13. The combination according to claim 6, wherein said reagent capillary comprises several several capillaries which several capillaries have a smaller cross-sectional area than said reagent capillary, said several capillaries, arranged horizontally relative each other and each comprising a single reagent.

14. The combination according to claim 13, wherein said several capillaries are provided in a multi lumen tube.

15. The combination according to claim 13, wherein said several capillaries are provided in a bundle as single thin capillaries bonded together.

16. The combination according to claim 13, wherein the inner diameter and length of said several capillaries corresponds to the desired reagent volume.

* * * * *